United States Patent
Lagrange et al.

(10) Patent No.: US 7,182,792 B2
(45) Date of Patent: Feb. 27, 2007

(54) COMPOSITION FOR DYEING KERATINOUS FIBERS COMPRISING AT LEAST ONE AZODIAZINE DIRECT DYE AND DYEING METHOD USING IT

(75) Inventors: Alain Lagrange, Coupvray (FR); Frédéric Guerin, Paris (FR); Sylvain Kravtchenko, Asnieres (FR)

(73) Assignee: L'Oreal S.A., Paris (FR)

( * ) Notice: Subject to any disclaimer, the term of this patent is extended or adjusted under 35 U.S.C. 154(b) by 389 days.

(21) Appl. No.: 10/902,086

(22) Filed: Jul. 30, 2004

(65) Prior Publication Data

US 2005/0091761 A1 May 5, 2005

Related U.S. Application Data

(60) Provisional application No. 60/509,944, filed on Oct. 10, 2003.

(30) Foreign Application Priority Data

Jul. 30, 2003 (FR) .................................. 03 50387

(51) Int. Cl.
*A61K 7/13* (2006.01)
(52) U.S. Cl. ........................ 8/405; 8/406; 8/407; 8/409; 8/410; 8/411; 8/412; 8/421; 8/425; 8/657; 8/689; 544/249
(58) Field of Classification Search .................... 8/405, 8/406, 407, 409, 410, 411, 412, 421, 425, 8/657, 689; 544/249
See application file for complete search history.

(56) References Cited

U.S. PATENT DOCUMENTS 2,528,378 A 10/1950 Mannheimer
2,781,354 A 2/1957 Mannheimer

FOREIGN PATENT DOCUMENTS

| DE | 197 46 137 | 4/1999 |
|---|---|---|
| EP | 1 166 754 | 1/2002 |
| EP | 1166754 A2 * | 2/2002 |
| FR | 1 285 848 | 4/1961 |

OTHER PUBLICATIONS

STIC Search Report dated Aug. 3, 2006.*
English language Derwent Abstract of DE 197 46 137, Apr. 22, 1999.

* cited by examiner

*Primary Examiner*—Eisa Elhilo
(74) *Attorney, Agent, or Firm*—Finnegan, Henderson, Farabow, Garrett & Dunner, LLP

(57) ABSTRACT

The present invention relates to a composition for dyeing keratinous fibers, containing at least one azodiazine direct dye corresponding to the following formula (I):

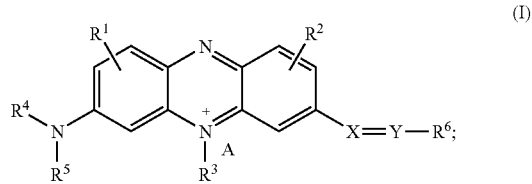

The present invention also relates to a method for dyeing keratinous fibers using these direct dyes.

31 Claims, No Drawings

COMPOSITION FOR DYEING KERATINOUS FIBERS COMPRISING AT LEAST ONE AZODIAZINE DIRECT DYE AND DYEING METHOD USING IT

This application claims benefit of U.S. Provisional Application No. 60/509,944, filed Oct. 10, 2003.

The present disclosure relates to compositions for dyeing keratinous fibers, such as human keratinous fibers, for example, hair, comprising at least one direct dye belonging to the azodiazine family.

It also relates to the use of certain compounds of the azodiazine family as direct dyes in compositions for dyeing keratinous fibers.

Finally, the present disclosure relates to methods for dyeing keratinous fibers using such compositions.

To dye keratinous fibers, such as the hair, it is known to use dyeing compositions containing oxidation dye precursors (e.g., ortho- or para-phenylenediamines, ortho- or para-aminophenols, generally called "oxidation bases") and optionally couplers (e.g., meta-phenylenediamines, meta-aminophenols and meta-diphenols, also called color modifiers). Oxidation dye precursors are colorless or faintly colored compounds which, when combined with oxidizing products (such as hydrogen peroxide) give rise, through an oxidation process, to colored and dyeing compounds.

However, methods for oxidation dyeing may have the following disadvantages:

- because of the use of oxidizing products such as hydrogen peroxide, they can cause degradation of the keratinous fibers and a bothersome irritation of the scalp;
- they may generate a fast color of the fibers, which may change over time and
- they may cause selectivity in the color of the fiber, i.e., differences in color along the same keratinous fiber.

To avoid the abovementioned disadvantages, it has been proposed to use direct dyes, which dye the hair by causing a colored molecule (the direct dye) to penetrate, by diffusion, into the hair without using hydrogen peroxide.

However, direct dyeing methods may also have disadvantages:

- they may cause insufficient color fastness, which color, for example, fades after a few shampoos;
- they too may cause selectivity in the color of the fibers, i.e., differences in color along the same keratinous fiber.

A true need therefore exists for a composition for dyeing keratinous fibers, which is not very selective, which can give a large variety of colors, intense colors and/or which additionally makes it possible to give a fast fiber color which changes little over time.

Thus, the present inventors have found that certain azodiazine compounds incorporated in compositions for dyeing keratinous fibers make it possible to overcome at least one of the disadvantages encountered in the prior art and make it possible to obtain a range of highly varied colors, a very low selectivity, and/or also a good level of fastness.

Accordingly, disclosed herein is a composition for dyeing keratinous fibers comprising at least one dye chosen from the compounds of the following formula (I):

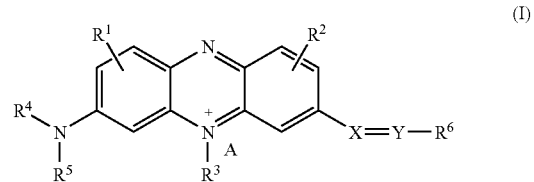

in which:

$R^1$ and $R^2$ are chosen, independently of each other, from:
a hydrogen atom;
alkyl groups comprising from 1 to 6 carbon atoms, wherein said alkyl groups may be optionally substituted with at least one group chosen from hydroxyl, amino, halogen, aryl, and C1 to C3 alkoxy groups;
aryl groups comprising from 6 to 18 carbon atoms, wherein said aryl groups may be optionally substituted with at least one group chosen from amino, hydroxyl, C1 to C3 alkoxy, and C1 to C6 alkyl groups;
carboxyalkyl groups comprising from 1 to 6 carbon atoms; and
sulphoalkyl groups comprising from 1 to 6 carbon atoms;

$R^3$ is chosen from a hydrogen atom, an optionally substituted alkyl group comprising from 1 to 6 carbon atoms, an optionally substituted alkenyl group, and an aryl group optionally substituted with at least one group chosen from hydroxyl, amino, halogen, C1 to C3 alkoxy, and C1 to C3 alkyl groups;

$R^4$ and $R^5$ are chosen from, independently of each other, a hydrogen atom, aryl groups, and alkyl groups comprising from 1 to 6 carbon atoms, wherein these groups may be optionally substituted with at least one group chosen from hydroxyl, cyano, halogen, amino, aryl, and C1 to C4 alkoxy groups;

$R^6$ is chosen from monocyclic and polycyclic groups comprising from 5 to 100 carbon atoms and optionally comprising at least one heteroatom and optionally comprising at least one unsaturation, wherein the mono- and polycyclic groups may be substituted with at least one group chosen from hydroxyl, halogen, amino, alkoxy, alkyl, and aromatic groups, provided that the group $R^6$ is not a phenol, aniline, diphenylamine, acylacetoarylamide, pyridone, quinoline, isoquinoline, pyrazole, indole, aminopyridine, pyrimidine, pyrimidone, naphthol, naphthylamine, aminothiazole, thiophene or hydroxylpyridine group;

X and Y are chosen from, independently of each other, a nitrogen atom and a group —CR' where R' is chosen from a hydrogen atom and an alkyl group comprising from 1 to 6 carbon atoms; and A is an anionic counterion;

As used herein, the expression "alkyl group" is generally understood to mean a linear or branched alkyl group of 1 to 6 carbon atoms, for example a methyl, ethyl, n-propyl, i-propyl, n-butyl, i-butyl or t-butyl group.

As used herein, the expression "alkoxy group" is generally understood to mean an —O-alkyl group, the term alkyl corresponding to the same definition as that given above.

The expression "alkenyl group," as used herein, is generally understood to mean a linear or branched alkenyl group of 2 to 20 carbon atoms.

Examples of alkenyl groups are vinyl, allyl and cyclohexenyl groups.

As used herein, the expression "aryl group" is generally understood to mean a monocyclic or polycyclic hydrocarbon aromatic group comprising from 6 to 18 carbon atoms, such as the phenyl group and the naphthyl group. This group may be optionally substituted with groups chosen from an amino group, a hydroxyl group, a C1 to C3 alkoxy group and a C1 to C6 alkyl group. Examples of substituted aryl groups are, for example, the 2-tolyl, 3-tolyl and 4-tolyl groups.

As used herein, the expression "carboxyalkyl group" is generally understood to mean an alkyl group as defined above, containing at the end a group —$CO_2H$, such as the carboxymethyl group —$CH_2$—$CO_2H$ and the carboxyethyl group —$(CH_2)_2$—$CO_2H$.

The expression "sulphoalkyl group," as used herein, is understood to mean an alkyl group as defined above, containing a sulphur atom forming a bridge between the above-mentioned alkyl group and the tricyclic unit of the compounds of formula (I).

As used herein, the expression "amino group" is generally understood to mean a group of formula —$NH_2$, optionally substituted on the nitrogen atom with one or two substituents such as alkyl groups comprising from 1 to 6 carbon atoms.

The expression "anionic counterion," as used herein, is understood to mean an anion capable of neutralizing the positive charge carried by the positively charged nitrogen atom of the tricyclic unit of the compounds of formula (I). This counterion may be a halide (such as a chloride, bromide, iodide), a sulphate, a methosulphate, a phosphate and a tosylate.

The expression "heteroatom," as used herein, is understood to mean an atom other than a carbon atom, such as an oxygen, nitrogen or sulphur atom.

According to one embodiment, $R^3$ may be chosen from an alkyl group optionally substituted with at least one group chosen, for example, from a hydroxyl group, a cyano group, a halogen group, an amino group, an aryl group, and an alkoxy group comprising from 1 to 4 carbon atoms. $R^3$ may also be chosen from an alkenyl group, as defined above, optionally substituted, for example, by at least one group chosen from a hydroxyl group, a cyano group, a halogen group, an amino group, an aryl group, an alkoxy group comprising from 1 to 4 carbon atoms, and an alkyl group. $R^3$ may also be chosen from an aryl group comprising from 6 to 18 carbon atoms, optionally substituted with at least one substituent chosen from a hydroxyl group, a halogen group, an amino group, a C1 to C3 alkoxy group, and a C1 to C3 alkyl group. By way of example, $R^3$ may be an optionally substituted phenyl group.

In one embodiment, the group $R^6$ as defined above is a cationic group. For example, such a group may be an optionally substituted group chosen from N—(C1–C4)alkylpyridinium, N—(C1–C4)alkylimidazolium, and N—(C1–C4)alkyltriazolium groups.

The compounds of formula (I) may be defined as direct dyes, that is to say they do not require developing with an appropriate agent as do oxidation dyes.

Among the compounds of formula (I) defined above, one may use the compounds of the following formulae (II) and (III), in which A is an anionic counterion, such as a chloride anion and W is also an anionic counterion, such as a chloride anion:

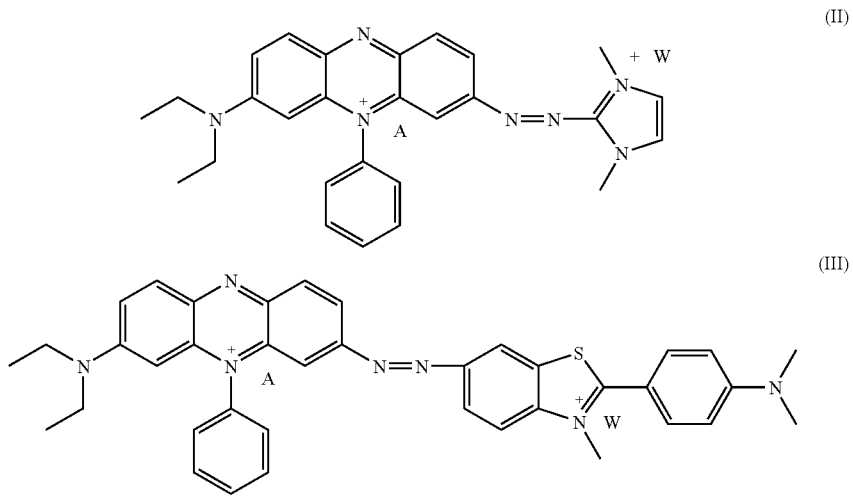

These dyes may be obtained by conventional synthesis schemes such as those described in Patent FR 1285848.

The dyes disclosed herein make it possible to obtain intense dyes on natural or optionally sensitized hair.

These dyes also make it possible to obtain varying glints which are chromatic or dark, very intense, not very selective and exhibit good fastness.

For example, the dyes disclosed herein make it possible to obtain neutral grey and black glints which change little over time.

The at least one dye of formula (I) is present in an amount ranging from 0.001 to 20% by weight, relative to the total weight of the dyeing composition, such as from 0.01 to 10% or from 0.1 to 5%.

The dyeing composition disclosed herein comprises, in one embodiment, an aqueous medium chosen from water or a mixture of water and a cosmetically acceptable organic solvent. There may be mentioned, by way of examples of cosmetically acceptable organic solvents, alcohols such as ethyl alcohol, isopropyl alcohol, and benzyl alcohol, polyols, polyol ethers, alkanes, ketones and mixtures thereof.

In addition, the composition may comprise at least one additional direct dye different from the compounds of formula (I) defined above. These additional direct dyes may be chosen from the direct dyes conventionally used in direct dyeing. There may be mentioned, among these dyes, commonly used aromatic and/or nonaromatic dyes such as nitro dyes, methines, azomethines, styriles, triarylmethanes, diarylmethanes, azo dyes, anthraquinone and naphthoquinone dyes, porphyrins, tetraphenylporphyrins, metalloporphyrins, phthalocyanines, natural dyes of the carotenoid, terpenoid and flavonoid type, and fluorescent dyes such as fluorescein, rhodamine and coumarin.

The composition disclosed herein may additionally comprise at least one oxidation base optionally combined with at least one coupler conventionally used for oxidation dyeing.

By way of examples of oxidation bases, there may be mentioned paraphenylenediamines, bisphenylalkylenediamines, para-aminophenols, ortho-aminophenols, and heterocyclic bases.

The couplers may be chosen from, for example, meta-phenylenediamine couplers, meta-aminophenol couplers, meta-diphenol couplers, naphthalenic couplers and heterocyclic couplers.

In addition to the dyes, the dyeing composition may also comprise the customary additives for dyeing compositions, such as additives chosen from surfactants, thickening agents, antioxidants, sequestering agents, dispersing agents, hair conditioners, preservatives, opacifying agents, acidifying agents, basifying agents and perfumes.

It is understood that persons skilled in the art will make an appropriate choice of these additives so that the advantageous properties of the composition which are inherent to the presence of the compounds of formula (I) as defined above are not impaired by the abovementioned additives.

The at least one surfactant which may be present in the composition may be chosen from anionic, nonionic, amphoteric and cationic surfactants.

Anionic, nonionic, amphoteric or cationic surfactants which are suitable for use herein include, but are not limited to, the following:

Anionic Surfactants:

By way of examples of anionic surfactants which can be used, alone or as mixtures, there may be mentioned salts, such as alkali metal salts (sodium salts, magnesium salts, ammonium salts, amine salts, amino alcohol salts and the like) of the following compounds: alkyl sulphates, alkyl ether sulphates, alkyl amidoether sulphates, alkyl aryl polyether sulphates, monoglyceride sulphates; alkyl sulphonates, alkyl phosphates, alkyl amide sulphonates, alkyl aryl sulphonates, α-olefin sulphonates, paraffin sulphonates; $(C_6–C_{24})$alkyl sulphosuccinates, $(C_6–C_{24})$alkyl ether sulphosuccinates, $(C_6–C_{24})$alkyl amide sulphosuccinates, $(C_6–C_{24})$alkyl sulphoacetates; $(C_6–C_{24})$acyl sarcosinates and $(C_6–C_{24})$acyl glutamates.

There may also be mentioned $(C_6–C_{24})$alkyl polyglycoside carboxylic esters such as alkyl polyglucoside citrates, alkyl polyglucoside tartrates, alkyl polyglucoside sulphosuccinates and alkyl polyglucoside sulphosuccinamates; acyl isethionates and N-acyltaurates, wherein the alkyl or acyl radical of all these compounds may comprise from 12 to 20 carbon atoms, and the aryl radical may be chosen from a phenyl or benzyl group.

Also capable of being used are the salts of fatty acids such as the salts of oleic, ricinoleic, palmitic and stearic acids, acids of copra oil or of hydrogenated copra oil; acyl lactylates whose acyl radical comprises from 8 to 20 carbon atoms; alkyl D-galactoside uronic acids and their salts; polyoxyalkylenated $(C_6–C_{24})$alkyl ether carboxylic acids, polyoxyalkylenated $(C_6–C_{24})$alkyl amidoether carboxylic acids and their salts, e.g., those comprising from 2 to 50 alkylene oxide, e.g., ethylene oxide, groups and mixtures thereof.

Nonionic Surfactants:

Useful nonionic surfactants are compounds which are well known per se and are described, for example, in the "Handbook of Surfactants", M. R. PORTER, Ed. Blackie & Son, Glasgow and London, 1991, 116–178.

Thus, used alone or as mixtures, they may be chosen, for example, from alcohols, α-diols, polyethoxylated and polypropoxylated alkylphenols having a fatty chain comprising, for example, from 8 to 18 carbon atoms, wherein the number of ethylene oxide or propylene oxide groups may range from 2 to 50; copolymers of ethylene oxide and propylene oxide, condensates of ethylene oxide and propylene oxide with fatty alcohols, polyethoxylated fatty amides having from 2 to 30 mol of ethylene oxide; polyglycerolated fatty amides comprising on average from 1 to 5, such as from 1.5 to 4, glycerol groups; oxyethylenated fatty acid esters of sorbitan comprising from 2 to 30 mol of ethylene oxide; fatty acid esters of sucrose, fatty acid esters of polyethylene glycol; alkyl polyglycosides; derivatives of N-alkyl glucamine and amine oxides such as $(C_{10}–C_{14})$alkyl amine oxides or N-acylaminopropylmorpholine oxides.

Amphoteric Surfactants:

The amphoteric (or zwitterionic) surfactants useful herein may be chosen, for example, alone or as mixtures, from the derivatives of aliphatic secondary or tertiary amines whose aliphatic radical is a linear or branched chain comprising from 8 to 18 carbon atoms and also comprising at least one water-solubilizing anionic group, for example a carboxylate, a sulphonate, a sulphate, a phosphate or a phosphonate.

There may also be mentioned $(C_8–C_{20})$alkyl betaines, sulphobetaines, $(C_8–C_{20})$alkyl amido$(C_1–C_6)$alkyl betaines and $(C_8–C_{20})$alkyl amido$(C_1–C_6)$alkyl sulphobetaines.

Among the amine derivatives, there may be mentioned the compounds marketed by the company Rhodia Chimie under the trade name Miranol®, which are described in U.S. Pat. Nos. 2,528,378 and 2,781,354 and which are classified in the CTFA Dictionary, 5$^{th}$ edition, 1993, under the names "disodium cocoamphodiacetate", "disodium lauroamphodiacetate", "disodium caprylamphodiacetate", "disodium capryloamphodiacetate", "disodium cocoamphodipropionate", "disodium lauroamphodipropionate", "disodium caprylamphodipropionate", "disodium capryloamphodipropionate", "lauroamphodiproponic acid" and "cocoamphodipropionic acid".

Cationic Surfactants:

As cationic surfactants which may be used alone or as mixtures, there may be mentioned the salts of optionally polyoxyalkylenated primary, secondary and tertiary fatty amines; quaternary ammonium salts such as tetraalkylammonium, alkylamidoalkyltrialkylammonium, trialkylbenzylammonium, trialkylhydroxylalkylammonium and alkylpyridinium chlorides and bromides; imidazoline derivatives and amine oxides having a cationic character.

The thickening agents which may be incorporated into the compositions disclosed herein may be of inorganic or organic origin. Among these, there may be mentioned thickening polymers of natural origin such as gums (xanthan gum, carob gum, guar gum), thickening polymers of synthetic origin (such as hydroxylethylcellulose, polyacrylic acids). Among these synthetic polymers, there may be mentioned associative polymers comprising a fatty chain, such as associative polymers of the acrylic or polyurethane type.

The pH of the dyeing composition generally ranges from 3 to 12, such as from 5 to 11, and such as from 6 to 10.

This pH may be adjusted to the desired value by virtue of the addition to the composition of acidifying or alkalinizing agents generally used in dyeing keratinous fibers or alternatively with the aid of conventional buffer systems.

Among the acidifying agents, there may be mentioned, by way of example, inorganic or organic acids such as hydrochloric acid, orthophosphoric acid, sulphuric acid, carboxylic acids such as acetic acid, tartaric acid, citric acid, lactic acid, and sulphonic acids.

Among the alkalinizing agents, there may be mentioned, by way of example, aqueous ammonia, alkali metal carbonates, alkanolamines such as mono-, di- and triethanolamines and derivatives thereof, sodium or potassium hydroxides and compounds of the following formula (IV):

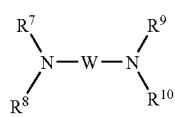

(IV)

wherein W is a propylene residue optionally substituted with a hydroxyl group or a $C_1$–$C_4$ alkyl radical; $R_7$, $R_8$, $R_9$ and $R_{10}$, which are identical or different, are chosen from a hydrogen atom, $C_1$–$C_4$ alkyl radicals, and $C_1$–$C_4$ hydroxylalkyl radicals.

The cosmetic composition may be provided in various galenic forms such as a lotion, a cream, a gel or any other appropriate form for dyeing keratinous fibers. It may also be packaged under pressure in an aerosol can in the presence of a propellant and can form a mousse.

The disclosure also relates to the use of compounds of formula (I) as defined above, as a direct dye in compositions for dyeing keratinous fibers, e.g., human keratinous fibers, such as the hair. These dyeing compositions have the same specifications as the compositions described above.

Finally, the disclosure relates to a method for the direct dyeing of keratinous fibers, comprising:

a) applying to the keratinous fibers a dyeing composition as defined above;

b) leaving the composition in the keratinous fibers for a sufficient leave-in time to obtain a desired color;

c) optionally rinsing the keratinous fibers so as to remove the dyeing composition therefrom;

d) optionally washing the keratinous fibers once or several times, rinsing them after each wash;

e) drying them.

Thus, the direct dyeing method comprises applying to the hair to be dyed the dyeing composition as defined above, and then leaving in, generally for a leave-in time of 3 to 60 minutes, e.g., of 5 to 40 minutes, such as 15 to 30 minutes, so as to give the composition time to properly act on the hair. This leave-in phase may be carried out at a temperature ranging from room temperature to 80° C., such as from 25 to 55° C.

Next, the keratinous fibers thus dyed are optionally rinsed in order to remove the dyeing composition which has reacted with the fibers and optionally washed once or several times.

When the dyeing composition contains at least one compound of formula (I) and at least one oxidation dye, as mentioned above, the dyeing method requires an additional step for developing, with an oxidizing agent, the color of the oxidation dye.

Consequently, the invention also relates to a method for dyeing keratinous fibers comprising:

f) applying to the keratinous fibers a dyeing composition comprising at least one compound of formula (I) as defined above and at least one oxidation dye, the color of the oxidation dye being developed with at least one oxidizing agent;

g) leaving the composition in the keratinous fibers for a sufficient leave-in time to obtain a desired color;

h) optionally rinsing the keratinous fibers to remove the dyeing composition therefrom;

i) optionally washing the keratinous fibers once or several times, rinsing them after each wash;

j) drying them.

The oxidizing agents which may be used are, for example, hydrogen peroxide, urea peroxide, alkali metal bromates, persalts such as perborates and persulphates, peracids and oxidase enzymes such as peroxidases, oxidoreductases containing two electrons such as uricases, and oxygenases containing four electrons such as laccases. In one embodiment, the oxidizing agent is hydrogen peroxide.

The at least one oxidizing agent may be added to the composition just at the time of use or it may be used from an oxidizing composition containing it.

In this embodiment, as above, the composition is left in, generally for 3 to 60 minutes, e.g., for 5 to 40 minutes, such as for 15 to 30 minutes, so as to give the composition enough time to properly act on the hair and for the development to take place. This leave-in phase may be carried out at a temperature ranging from room temperature to 80° C., such as from 25 to 55° C.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The invention will now be described in relation to the following examples, given by way of illustration and without limitation.

EXAMPLE 1

A dyeing composition 1 having the constituents described in Table 1 below was prepared. This composition comprises a dye (1) (molecular weight: 488 g/mol) in accordance with the present disclosure:

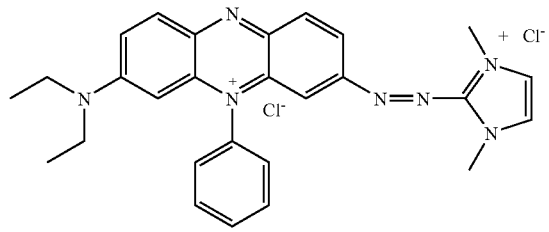

TABLE 1

| Constituents | Quantity |
| --- | --- |
| Dye (1) | 0.49 g |
| Benzyl alcohol | 4 g |
| Polyethylene glycol 6 EO | 6 g |
| Hydroxylethylcellulose | 0.7 g |
| Alkyl polyglucoside as an aqueous solution containing 60% AM* | 4.5 g AM* |
| Phosphate buffer | qs pH 7 |
| Demineralized water | qs 100 g |

*AM: Active material.

EXAMPLE 2

A dyeing composition 2 having the constituents described in Table 2 below was prepared. This composition comprises a dye (2) (molecular weight: 660 g/mol) in accordance with the present disclosure:

TABLE 2

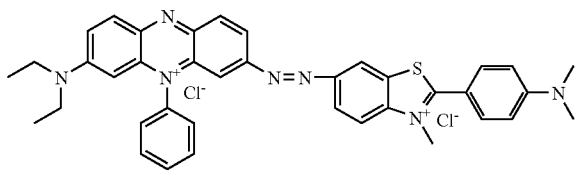

| Constituents | Quantity |
| --- | --- |
| Dye (2) | 0.66 g |
| Benzyl alcohol | 4 g |
| Polyethylene glycol 6 EO | 6 g |
| Hydroxylethylcellulose | 0.7 g |
| Alkyl polyglucoside as an aqueous solution containing 60% AM* | 4.5 g AM* |
| Phosphate buffer | qs pH 7 |
| Demineralized water | qs 100 g |

*AM: Active material.

What is claimed is:

1. A composition for dyeing keratinous fibers comprising at least one direct dye chosen from compounds of the following formula (I):

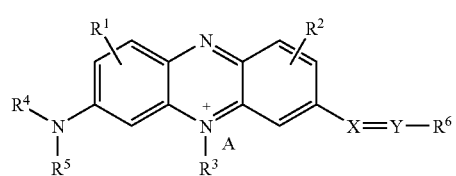

wherein:

$R^1$ and $R^2$, independently of each other, are chosen from:
a hydrogen atom;
alkyl groups comprising from 1 to 6 carbon atoms and optionally substituted with at least one group chosen from hydroxyl, amino, halogen, aryl, and C1 to C3 alkoxy groups;
aryl groups comprising from 6 to 18 carbon atoms and optionally substituted with at least one group chosen from amino, hydroxyl, C1 to C3 alkoxy, and C1 to C6 alkyl groups;
carboxyalkyl groups comprising from 1 to 6 carbon atoms; and
sulphoalkyl groups comprising from 1 to 6 carbon atoms;

$R^3$ is chosen from a hydrogen atom, an optionally substituted alkyl group comprising from 1 to 6 carbon atoms, an optionally substituted alkenyl group, and an aryl group optionally substituted with at least one group chosen from hydroxyl, amino, halogen, C1 to C3 alkoxy, and C1 to C3 alkyl groups;

$R^4$ and $R^5$ are chosen from, independently of each other, a hydrogen atom, aryl groups and alkyl groups comprising from 1 to 6 carbon atoms, said groups being optionally substituted with at least one group chosen from hydroxyl, cyano, halogen, amino, aryl, and C1 to C4 alkoxy groups $R^6$ is chosen from mono- and polycyclic groups comprising from 5 to 100 carbon atoms and optionally at least one heteroatom and optionally at least one unsaturation, wherein said mono- and polycyclic groups may be substituted with at least one group chosen from hydroxyl, halogen, amino, alkoxy, alkyl, and aromatic groups, provided that the group $R^6$ is not a phenol, aniline, diphenylamine, acylacetoarylamide, pyridone, quinoline, isoquinoline, pyrazole, indole, aminopyridine, pyrimidine, pyrimidone, naphthol, naphthylamine, aminothiazole, thiophene or hydroxylpyridine group;

X and Y are chosen from, independently of each other, a nitrogen atom and a group CR' wherein R' is chosen from a hydrogen atom or an alkyl group comprising from 1 to 6 carbon atoms; and A is an anionic counterion.

2. A dyeing composition according to claim 1, wherein the group $R^6$ is a cationic group.

3. A dyeing composition according to claim 1, wherein $R^6$ is chosen from a N—(C1–C4)alkylpyridinium group, an N—(C1–C4)alkylimidazolium group, and an N—(C1–C4) alkyltriazolium group.

4. A dyeing composition according to claim 1, wherein the at least one direct dye is chosen from compounds of the following formulae (II) and (III):

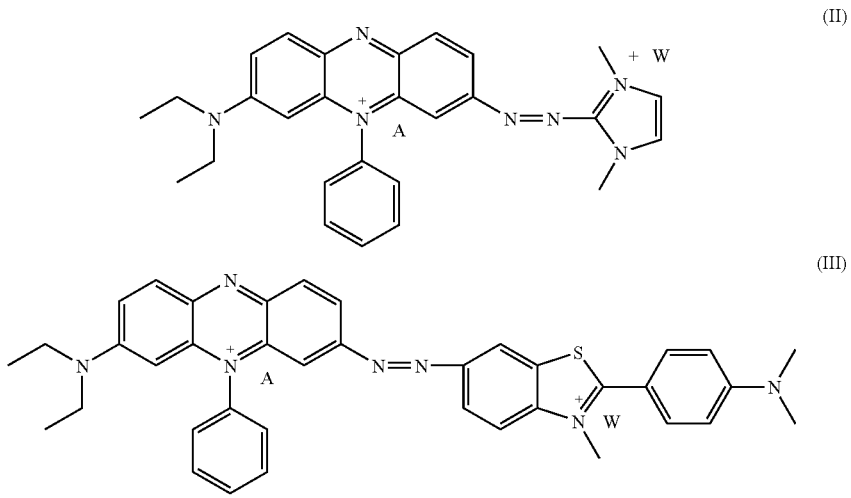

wherein A is an anionic counterion and W is also an anionic counterion.

5. A dyeing composition according to claim 4, wherein A and W are both chloride ions.

6. A dyeing composition according to claim 1, wherein the at least one direct dye is present in an amount ranging from 0.001 to 20% by weight relative to the total weight of the composition.

7. A dyeing composition according to claim 6, wherein the at least one direct dye is present in an amount ranging from 0.01 to 10% by weight relative to the total weight of the composition.

8. A dyeing composition according to claim 7, wherein the at least one direct dye is present in an amount ranging from 0.1 to 5% relative to the total weight of the composition.

9. A dyeing composition according to claim 1, comprising an aqueous medium chosen from water and a mixture of water and at least one cosmetically acceptable organic solvent.

10. A dyeing composition according to claim 9, wherein the at least one cosmetically acceptable organic solvent is chosen from alcohols, polyols, polyol ethers, alkanes, and ketones.

11. A dyeing composition according to claim 10, wherein the alcohols are chosen from ethyl alcohol, isopropyl alcohol, benzyl alcohol, and mixtures thereof.

12. A dyeing composition according to claim 1, additionally comprising at least one additional direct dye different from the compounds of formula (I) as defined in claim 1.

13. A dyeing composition according to claim 12, wherein the at least one additional direct dye is chosen from nitro dyes, methines, azomethines, styriles, triarylmethanes, diarylmethanes, azo dyes, anthraquinone and naphthoquinone dyes, porphyrins, tetraphenylporphyrins, metalloporphyrins, phthalocyanines, natural dyes of the carotenoid, terpenoid and flavonoid type, and fluorescent dyes.

14. A dyeing composition according to claim 13, wherein the fluorescent dyes are chosen from fluorescein, rhodamine and coumarin.

15. A dyeing composition according to claim 1, additionally comprising at least one oxidation base optionally combined with at least one coupler.

16. A dyeing composition according to claim 15, wherein the at least one oxidation base is chosen from para-phenylenediamines, bisphenylalkylenediamines, para-aminophenols, ortho-aminophenols and heterocyclic bases.

17. A dyeing composition according to claim 15, wherein the at least one coupler is chosen from meta-phenylenediamine couplers, meta-aminophenol couplers, meta-diphenol couplers, naphthalenic couplers and heterocyclic couplers.

18. A dyeing composition according to claim 1, additionally comprising at least one additive chosen from surfactants, thickening agents, antioxidants, sequestering agents, dispersing agents, hair conditioners, preservatives, opacifying agents, adidifying agents, basifying agents and perfumes.

19. A dyeing composition according to claim 1, said composition having a pH ranging from 3 to 12.

20. A dyeing composition according to claim 19, wherein said pH ranges from 5 to 11.

21. A dyeing composition according to claim 20, wherein said pH ranges from 6 to 10.

22. A method for the direct dyeing of keratinous fibers, comprising:

applying to the keratinous fibers a dyeing composition comprising at least one direct dye chosen from compounds of the following formula (I):

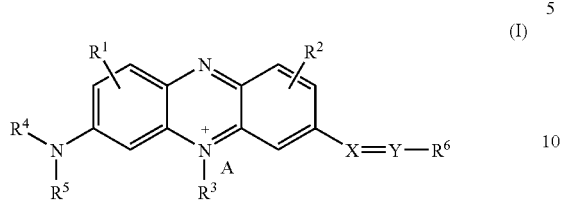

wherein:
R¹ and R², independently of each other, are chosen from:
a hydrogen atom;
alkyl groups comprising from 1 to 6 carbon atoms and optionally substituted with at least one group chosen from hydroxyl, amino, halogen, aryl, and C1 to C3 alkoxy groups;
aryl groups comprising from 6 to 18 carbon atoms and optionally substituted with at least one group chosen from amino, hydroxyl, C1 to C3 alkoxy, and C1 to C6 alkyl groups;
carboxyalkyl groups comprising from 1 to 6 carbon atoms; and
sulphoalkyl groups comprising from 1 to 6 carbon atoms;
R³ is chosen from a hydrogen atom, an optionally substituted alkyl group comprising from 1 to 6 carbon atoms, an optionally substituted alkenyl group, and an aryl group optionally substituted with at least one group chosen from hydroxyl, amino, halogen, C1 to C3 alkoxy, and C1 to C3 alkyl groups;
R⁴ and R⁵ are chosen from, independently of each other, a hydrogen atom, aryl groups and alkyl groups comprising from 1 to 6 carbon atoms, said groups being optionally substituted with at least one group chosen from hydroxyl, cyano, halogen, amino, aryl, and C1 to C4 alkoxy groups;
R⁶ is chosen from mono- and polycyclic groups comprising from 5 to 100 carbon atoms and optionally at least one heteroatom and optionally at least one unsaturation, wherein said mono- and polycyclic groups may be substituted with at least one group chosen from hydroxyl, halogen, amino, alkoxy, alkyl, and aromatic groups, provided that the group R⁶ is not a phenol, aniline, diphenylamine, acylacetoarylamide, pyridone, quinoline, isoquinoline, pyrazole, indole, aminopyridine, pyrimidine, pyrimidone, naphthol, naphthylamine, aminothiazole, thiophene or hydroxylpyridine group;
X and Y are chosen from, independently of each other, a nitrogen atom and a group CR' wherein R' is chosen from a hydrogen atom or an alkyl group comprising from 1 to 6 carbon atoms; and
A is an anionic counterion;
leaving the composition on the keratinous fibers for a sufficient time to obtain a desired color;
optionally rinsing the keratinous fibers to remove the dyeing composition therefrom;
optionally washing the keratinous fibers once or several times, rinsing them after each wash; and
drying them.

23. A method for dyeing keratinous fibers comprising:
applying to the keratinous fibers a dyeing composition comprising at least one oxidation dye and at least one direct dye chosen from compounds of formula (I), and developing the color of the oxidation dye with at least one oxidizing agent:

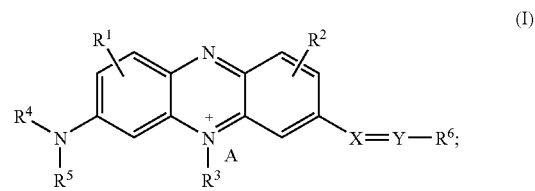

wherein:
R¹ and R² independently of each other, are chosen from:
a hydrogen atom;
alkyl groups comprising from 1 to 6 carbon atoms and optionally substituted with at least one group chosen from hydroxyl, amino, halogen, aryl, and C1 to C3 alkoxy groups;
aryl groups comprising from 6 to 18 carbon atoms optionally substituted with at least one group chosen from amino, hydroxyl, C1 to C3 alkoxy, and C1 to C6 alkyl groups;
carboxyalkyl groups comprising from 1 to 6 carbon atoms; and
sulphoalkyl groups comprising from 1 to 6 carbon atoms;
R³ is chosen from a hydrogen atom, an optionally substituted alkyl group comprising from 1 to 6 carbon atoms, an optionally substituted alkenyl group, and an aryl group optionally substituted with at least one group chosen from hydroxyl, amino, halogen, C1 to C3 alkoxy, and C1 to C3 alkyl groups;
R⁴ and R⁵ are chosen from, independently of each other, a hydrogen atom, aryl groups and alkyl groups comprising from 1 to 6 carbon atoms, said groups being optionally substituted with at least one group chosen from hydroxyl, cyano, halogen, amino, aryl, and C1 to C4 alkoxy groups;
R⁶ is chosen from mono- and polycyclic groups comprising from 5 to 100 carbon atoms and optionally at least one heteroatom and optionally at least one unsaturation, wherein said mono- and polycyclic groups may be substituted with at least one group chosen from hydroxyl, halogen, amino, alkoxy, alkyl, and aromatic groups, provided that the group R⁶ is not a phenol, aniline, diphenylamine, acylacetoarylamide, pyridone, quinoline, isoquinoline, pyrazole, indole, aminopyridine, pyrimidine, pyrimidone, naphthol, naphthylamine, aminothiazole, thiophene or hydroxylpyridine group;
X and Y are chosen from, independently of each other, a nitrogen atom and a group CR' wherein R' is chosen from a hydrogen atom and an alkyl group comprising from 1 to 6 carbon atoms; and
A is an anionic counterion;
leaving the composition on the keratinous fibers for a sufficient time to obtain a desired color;
optionally rinsing the keratinous fibers to remove the dyeing composition therefrom;

optionally washing the keratinous fibers once or several times, rinsing them after each wash; and
drying them.

24. A method according to claim 23, wherein the leave-in time ranges from 3 to 60 minutes.

25. A method according to claim 24, wherein the leave-in time ranges from 5 to 40 minutes.

26. A method according to claim 25, wherein the leave-in time ranges from 15 to 30 minutes.

27. A method according to claim 23, wherein the at least one oxidizing agent is chosen from hydrogen peroxide, urea peroxide, alkali metal bromates, persalts, peracids and oxidase enzymes, oxidoreductases containing two electrons, and oxygenases containing four electrons.

28. A method according to claim 27, wherein the persalts are chosen from perborates and persulphates.

29. A method according to claim 27, wherein the oxidase enzymes are chosen from peroxidases.

30. A method according to claim 27, wherein the oxidoreductases containing two electrons are chosen from uricases.

31. A method according to claim 27, wherein the oxygenases containing four electrons are chosen from laccases.

* * * * *